Figure 1:
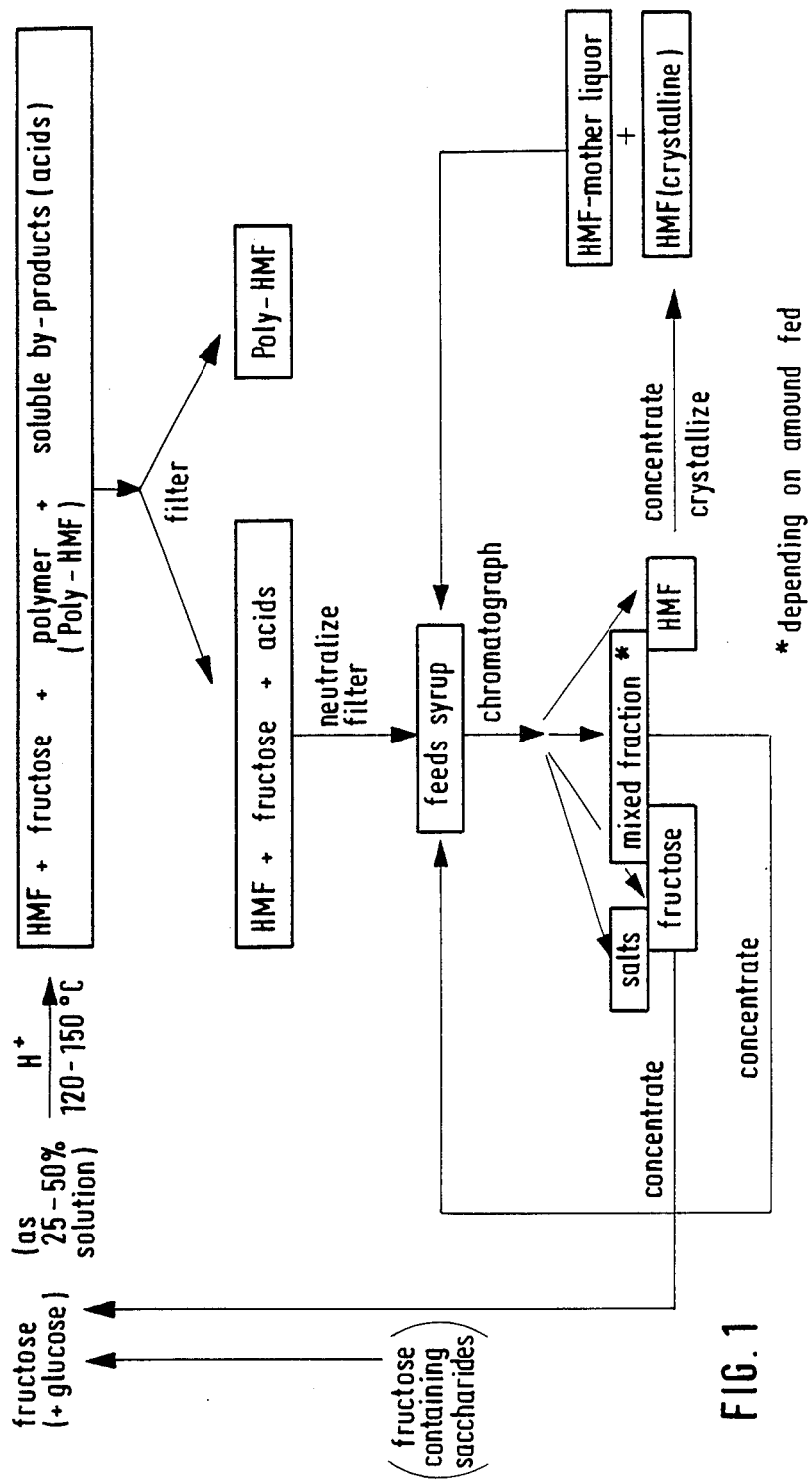

United States Patent [19]

Rapp

[11] Patent Number: 4,740,605

[45] Date of Patent: Apr. 26, 1988

[54] PROCESS FOR PREPARING PURE 5-HYDROXYMETHYLFURFURALDEHYDE

[75] Inventor: Knut M. Rapp, Offstein, Fed. Rep. of Germany

[73] Assignee: Suddeutsche Zucker-Aktiengesellschaft, Fed. Rep. of Germany

[21] Appl. No.: 2,340

[22] Filed: Jan. 12, 1987

[30]  Foreign Application Priority Data

Jan. 17, 1986 [DE]  Fed. Rep. of Germany ....... 3601281

[51] Int. Cl.$^4$ ............................................ C07D 307/50
[52] U.S. Cl. .................................................. 549/483
[58] Field of Search ........................................ 549/483

[56]  References Cited

U.S. PATENT DOCUMENTS 2,776,948  1/1957  Snyder ............................ 549/483 X
2,929,823  3/1966  Garber ................................ 549/483

FOREIGN PATENT DOCUMENTS 3033527  4/1981  Fed. Rep. of Germany .
3309564  9/1984  Fed. Rep. of Germany .

OTHER PUBLICATIONS

Bonner et al, J. Chem. Soc., (1960), pp. 787–791.
Szamt et al, J. Chem. Tech. Biotechnol, vol. 31 (1981), pp. 135–145.
Brown et al, J. Chem. Tech. Biotechnol, vol. 32 (1982), pp. 920–924.
Fayst et al, Carbohydrate Research, vol. 122 (1983), pp. 59–68.

Primary Examiner—Richard L. Raymond
Attorney, Agent, or Firm—Armstrong, Nikaido, Marmelstein & Kubovcik

[57]  ABSTRACT

The present invention refers to a process for preparing 5-hydroxymethylfurfuraldehyde, which is also called HMF. This compound was yet prepared by dehydration of fructose-containing carbohydrates in the presence of various catalysts. Nevertheless, the separation of HMF from starting material, by-products and organic solvents was difficult and disadvantageous, especially by the presence of organic solvents. Surprisingly, it came out, that it is possible, to separate 5-hydroxymethylfurfuraldehyde from reaction mixtures, which are obtained by reactions of saccharides with an acid catalyst, in great purity and good yield with exclusive utilization of water as solvent, by means of ion exchangers, and to crystallize it out from chromatographic fractions.

10 Claims, 2 Drawing Sheets

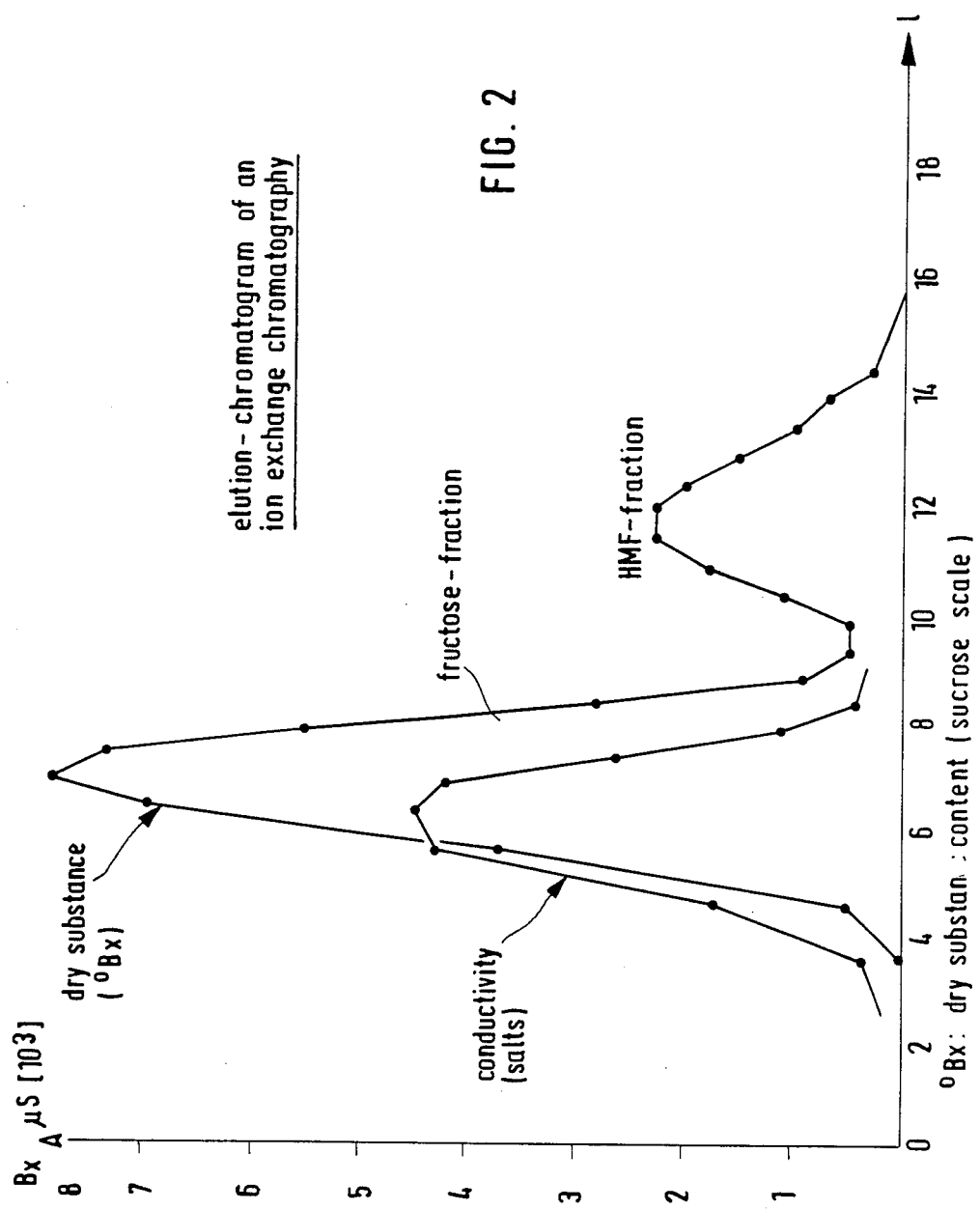

PROCESS FOR PREPARING PURE 5-HYDROXYMETHYLFURFURALDEHYDE

Description

An intramolecular, threefold dehydration product of hexoses is 5-hydroxymethylfurfuraldehyde (in the following named HMF) with the general formula

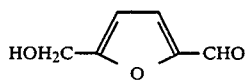 I

Agricultural raw materials, e.g. starch, cellulose, sucrose or inulin are low-priced starting products for the manufacture of hexoses, like glucose and fructose. HMF has, among other things antibacterial and anticorrosive properties and is suitable for a variety of reactions. It is possible, without any difficulty, to make from it furfuryldialcohol, -dialdehyde, and -dicarboxylic acid and derivatives thereof; as well, the hydrogenation of the ring leads to difunctional 2,5-tetrahydrofuran-derivatives. At C-2 and C-5 differently substituted, difunctional furanderivatives are also well accessible from HMF. Basically, HMF is an intermediate in the dehydrative decomposition of hexoses to levulinic and formic acid, i.e. it crucially depends on, to stop the reaction at the right moment. So, the separation of HMF from the starting carbohydrates and by-products is the essential step for it production.

Beside fructose, especially fructose-containing carbohydrates like sucrose, fructose syrups e.g. "high fructose corn syrup" (HFCS, Isoglucose), mother liquors of the crystallization of fructose or polymeric fructosides, like inulin, are suitable as starting material for a practicable manufacture of HMF, also on large scale.

Even the inulin-containing chicory (inulin-content app. 18 %) is suitable for the preparation of a fructose- and HMF-containing mixture, even as pure mash or in admixture with water.

Since glucose, as well in polymeric form, starch or cellulose, is synthesized by photosynthesis in nearly unlimited amounts, and an isomerization of glucose to fructose is practible in largest scale, the starting material for the synthesis of HMF is easy available in great amounts.

As especially appropriate primary material for the production of HMF, mother liquors of the crystallization of fructose should be mentioned.

As catalysts for dehydration are described several acids or salts, e. g. oxalic acid (cp. W. N. Haworth et al.; J. Chem. Soc. 1944, 667), salts like pyridine hydrochloride (cp. C. Fayet et al., Carbohydr. Res. 122, 59 (1983)), ion exchangers in H+-form (cp. DE-OS No. 30 30 33 527) or Lewis acids, like zirconyl chloride (cp. SU No. 1 054 349, quoted in CA 100, 120 866 s) or boron trifluoride etherate (cp. H. H. Szmant et al., J. Chem. Tech. Biotechnol. 31, 135 (1981)).

For the large-scale HMF-production the applied catalyst should be good value and non-corrosive. Solid, for reuse determined, catalysts are unsuitable, because insoluble byproducts are formed easily and the separation of the catalyst (e.g. ion exchangers) from these by-products is unecomonical resp. impossible. Lewis acids, like zirconyl chloride or aluminium chloride, have to be disapproved too of reasons concerning the corrosiveness. Therefore, the use of sulphuric acid or phosphoric acid is considered to be advantageous, because in this case the aqueous acid reaction mixtures can if desired be neutralized with bases and, if calcium hydroxide or calcium carbonate is used, the acid catalyst is converted in salts of low solubility and removed by filtration.

The medium of the dehydration reaction of saccharides is determined by their solubility. Amongst water, especially dipolar, aprotic solvents were used, e.g. dimethylformamide or dimethylsulfoxyde.

The iodine-catalyzed conversion of the fructose part in sucrose to HMF by heating sucrose in water-free dimethylformamide requires, besides the expensive solvent, a complicated working up, namely extraction and paper chromatography (cp T. G. Bonner et al., J. Chem. Soc. 1960, 787).

In dimethylsulfoxyde good yields (>90%) can be found, if fructose is decomposed with different catalysts (cp. e.g. H. H. Szmant et al., J. Chem. Tech. Biotechnol. 31, 135 (1981)). The isolation of the desired product is, of course among other things, difficult, because of the high boiling point of the solvent, and this makes a repeated extraction necessary.

In the DE-OS No. 33 09 564 therefore a derivatisation to 5-acetoxymethylfurfuraldehyde is proposed for the isolation of HMF from dimethylsulfoxyde-containing mixtures.

This requires, however, in addition to a vacuum distillation two reaction steps (acetylation, deacetylation) and therefore, expenditure of time and chemicals.

Several methods utilize mixtures of water and organic solvents in the reaction medium. In U.S. Pat. No. 2,929,823 furfural is added to solutions of saccharides in water and the mixture is heated tp 250°-380° C. for a short time (0.1–120 sec.) Tarry by-products are solubilized by the added organic solvent, just as HMF. The preparation of HMF in a pure state seems difficultly practicable in this way.

Another two-phase procedure is described in DE-OS No. 30 33 527. Here, under milder conditions (below 100° C.) fructose-containing aqueous solutions are decomposed with acid ion-exchangers, in the presence of an organic water-immiscible solvent, which, however, has a high dissolving-ability for HMF. The great drawback of this procedure consists in the necessity, to use a big surplus of the organic solvent, referred to the aqueous phase (>7:1), and that the required solvents are expensive and toxic. In addition, the very good solubility of HMF in water makes every extraction of the product from aqueous solutions with organic solvents extremely difficult.

In the publication of C. Fayet et al., Carbohydr. Res. 122, 59 (1983) is the decomposition of saccharides without solvent described, but with equimolar amounts of catalyst. However, the catalyst, pyridine hydrochloride, is unsuitable for the industrial application of this method. Moreover, after addition of water, it follows a time-consuming extraction (20 h) with ethylacetate.

As the above-mentioned examples show, the greatest problem in the production of HMF is, especially in a larger scale, to separate the product from starting materials, by-products and solvents. This is expressed also in the publication of D. W. Brown et al.; J. Chem. Tech. Biotechnol. 32, 920 (1982), where accordingly is said, that the newer methods of HMF-preparation have the disadvantage, that the product is dissolved in aqueous solution or in a polar solvent, from which the isolation is difficult.

Therefore, it was unexpected, that just the existence of HMF in aqueous solution has an exceptional advantage and that it is possible, with exclusive utilization of water as solvent, to prepare HMF in great purity and good yield.

The use of expensive and dangerous organic solvents, time-consuming extraction procedures with difficult phase separations, high-vacuum distillations with the risk of decomposition are absolutely missing, because in the inventive process not only the reaction can be done in water, but also especially the work-up (separation) and the crystallization of HMF can be accomplished in water. In addition, the inventive process shall not exclude processes of such a kind, in which the reaction, eventually with added organic solvents, leads to saccharide/HMF-mixtures, but an isolation of HMF, after removal of the organic solvent, results from a chromatography with water as eluent.

If one considers, how complex a multiple dehydration from a hexose proceeds, and that from both, fructose and the reaction product HMF, so-called humic matter is formed, some soluble, some insoluble, so it is surprising, that HMF results in such a high purity from the applied chromatography.

Surprising too, was the amount of reaction product, which can be separated per volume of resin on the chromatographic column. While the amount of monosaccharides often comes to app. 2 % of the bed volume, it is possible in the case of fructose/HMF-mixtures to separate up to twice the dry matter quantity per resin volume completely i.e. without mixed fractions.

Unexpected simple is in the inventive process the separation of insoluble by-products. Polymers, which are called in the literature "humic matter", are formed as by-products of dehydrating reactions of carbohydrates. These can result in different forms, so e.g. as tar (U.S. Pat. No. 2,929,823), as fine powder, or as in the present inventive process, with application of solutions of fructose and oxalic or sulphuric acid as catalyst, in form of a pearl polymer (here called Poly-HMF).

These solids have an elementary analysis of app. $C=63\%$, $H=4\%$ and $O=33\%$ and can be filtered very easily owing to their grain size of app. 1 mm diameter; they possess interesting properties and are therefore a valuable byproduct of the inventive process.

The starting material, e.g. a fructose syrup with 89% fructose in the dry matter (remainder: glucose 9% and oligosaccharides), is brought in an autoclave as 25-50 % solution and with the catalytic acid adjusted to pH 1,8. The mixture is heated under stirring (speed 120 r.p.m.) to 120°-150° C. and held app. 2 hours at this temperature. Subsequently is cooled.

If the, as by-product formed, pearl polymer (Poly-HMF) should be isolated, it is filtered off, otherwise, the reaction mixture is neutralized with a base and the combined unsoluble precipitate is filtered off. It is advantageous, to add such cations, which are present on the ion-exchanger of the following chromatography as counter-ions, i.e. one should neutralize with calcium hydroxyde or calcium carbonate, if the used loading form of the exchanger resin is the $Ca^{2+}$-form (e.g. Lewatit TSW 40, $Ca^{2+}$-form, as strong acid gel-type cation exchanger on basis of polystyrene sulfonic acid, crosslinked with app. 4% divinyl benzene). Other resins are not excluded by the inventive process.

If the reaction mixture is not neutralized, it is possible, after filtration, to chromatograph the mixture directly over columns of exchanger resins in $H^+$-form.

In this case, separations are accomplished with such different resins as e.g. strongly acidic, highly crosslinked, macroporous cation exchangers on polystyrene sulfonic acid basis (e.g. Lewatit SP 112), weakly acidic, macroporous cation exchangers on polyacrylate basis (e.g. Lewatit CNP LF) or weakly crosslinked, gel-type cation exchange resins (e.g. Lewatit TSW 40).

On every resin, coloured and acidic by-products are separated from HMF, which is eluted after the saccharides (fructose).

The amount of reaction mixture to be separated is in the range of 10% of the resin bed volume (feedsyrup with app. 35% d.s.).

The filtered solution is used advantageously direct, without concentration or dilution, as feedsyrup for the chromatography. This has especially process-technical advantages, if great amounts are worked with. In the chromatography, it is possible, to use up to 20% of the resin bed volume as feeding volume in form of an app. 30% (d.s.) solution. Water is applied as eluent with a linear flowrate of app. 3.2 cm/min in the resin bed. A temperature of app. 55°-85° C. is favourable for the separation.

Depending on the amount of mixture to separate, one can get the separation in HMF- and saccharide-fraction without or with a mixed fraction.

When charging the column with app. 8 % of the bedvolume, (33,2 % d.s.), the elution can be devided in fore-runnings, which contain a part of the salts, coloured substances and glucose.

The first product fraction contains the main part of fructose, the following second product fraction contains HMF;

In this fraction practically no salts are found. The concentration of this fraction yields an amber syrup, which crystallizes in short time at temperatures below 20° C. and a purity >90%. This purity is sufficient for many applications.

This syrup can be refined, either by means of crystallization by cooling, either by isothermal crystallization below 20° C., with simultaneous decrease of the remaining water content by vacuum evaporation. In both cases one gets analytically pure HMF.

The essentially fructose-containing fraction can be reacted after concentration again in the autoclave or be used as diluent for higher concentrated saccharide mixtures.

A mixed fraction, which is obtained when larger feeding amounts are separated, can be rechromatographed or used as such. In FIG. 1 is shown a flowchart of the HMF preparation; in FIG. 2 is shown an elution chromatogram (exp. 5).

The chromatographed concentrated HMF-containing syrup (water content <20%, temperature during vacuum-concentration <80° C.) is crystallized by cooling; the syrup is cooled, at first, rapidly to 20° C. in a suitable stirred cooler-crystallizer. The further cooling takes place with a cooling-rate of 2-20 °/h, predominantly 2-5 °/h.

At this resulting temperature of oversaturation, which depends on the water-content, e.g. 10° C., the mass is seeded with crystals of HMF and cooling in continued to such a temperature, that the amount of crystals in the magma reaches 55-60%.

At this temperature, the crystals are separated from the mother liquor by means of a centrifugal separator or a pressure filter. The so obtained crystals have a purity of >97%.

The resulting mother liquor is crystallized for a second crop and, as described above, crystals and mother liquor are separated. The non-crystalline part of this second crystallization is rechromatographed.

The crystals of the first and second crystallization are liquefied by raising the temperature, filtered and crystallized, as mentioned above.. In this way analytically pure HMF (purity >99%) is prepared.

The feeding amount for the chromatography can be choosen especially high, if the chromatographic equipment consists of several colums. This is not only advantageous from spacial reasons in large-scale facilities, but also makes it possible, in a multi-column construction, to lead out a part of the elution stream, at a suitable position and, to lead only the remainder through the entire system.

In the decribed inventive process a three-column-equipment was applied, whereby the columns, with equal resin content each, one after the other, are flowed through.

The outflow from the first two columns is led in a separate tank, as long as in the outlet of column 2 the dry matter maximum is exceeded (refractive index). Just then, the elution stream is led via a valve on column 3 and the chromatography is continued (fractionated) in the usual manner.

In a three-column-equipment (total length: 10 m, diameter: 25 cm), which contains e.g. the above mentioned cation exchange resin TSW 40 in $Ca^{2+}$-form, it is possible, to separate e.g. 120 kg of a reaction mixture (7,8 % HMF) in such a way, that only HMF-containing solutions are led on to the third column and are separated on this, for the most part, completely from fructose.

EXAMPLE 1

11 kg fructose are dissolved in 33 l water and 110 g oxalic acid is added. This mixture is heated in a stirrer autoclave (speed 120 r.p.m.) in 15 min to 140° C. and, after holding for 130 min at a temperature between 135°–142° C., is cooled to 40° C. The formed solids (Poly-HMF) are filtered off in a pressure filter (1.3 kg; according to the elementary analysis, this corresponds to a dehydration of 2.05 kg fructose) and the filtrate is neutralized with calcium carbonate (pH 5) and filtered. The filtrate (41.0 kg) contains 6.3% HMF, this is equivalent to 2.58 kg HMF, which are formed from 3.7 kg fructose. Referred to the initial fructose, the yield is 33.6%. The solution contains still 4.3 kg unchanged fructose. The yield, related to total transformed fructose, is hence 55%. Besides HMF and fructose, small amounts of glucose and oligosaccharides are present, and after filtration of insoluble Poly-HMF, soluble high-molecular humic substances, which can be separated totally from HMF in the following chromatography.

EXAMPLE 2

20 kg chicory roots with an inulin content of 17.8% (measured as fructose after enzymatic hydrolysis) are ground to a mash. This is mixed with 20 kg water, and with sulphuric acid the pH value is brought to 1.8 (1.3 kg of 20% $H_2SO_4$). The acidified mash is heated in a stirrer autoclave within 15 min to 140° C., and held 2 h at this temperature (pressure 7.2 bar), then cooled to 70° C. and then filtered in a pressure filter. Besides a residue weighing 7.5 kg (d.s.), one gets a solution (32 kg) with the following analysis (rel. on d.s.): HMF=16.6%, fructose=59.5%, glucose=7.2%, remainder=16.7%. This corresponds to the following amounts: 298 g HMF (≙ 426 g transformed fructose), 1062 g fructose, 131 g glucose and 304 g other saccharides.

Related to the determined quantity of inulin in 20 kg chicory roots, i.e. 3.3 kg, the HMF-yield comes to 13%, the isolable quantity of fructose is 30%. The filtrate is brought to pH 6.5 with 380 g calcium carbonate and filtered again.

EXAMPLE 3

Chipped chicory roots are extracted in a counter current extraction apparatus (DDS-extractor) with water at 70° C. (in counter current); a crude extract is obtained, which contains 16 % inulin, and which is concentrated to 30% d.s. The yield of inulin, referred to soluble dry substance in the parts of the plant, is 86.8%. The decomposition in the autoclave is made analogous to example 1.

EXAMPLE 4

Ground chicory roots are mixed homogenously with 20% sulphuric acid (ratio: 34 ml sulphuric acid/kg chicory mash) and held for 2.5 h at a temperature of 80 ° C. Analogous to the Henze-pressure boiler the mass is further disintegrated in a prewarmed pressure nutsche filter by introducing steam with 6 bar pressure for 1 hour. After that, the pressure is expanded and the liquefied mass is brought directly, or after filtration, into an autoclave and reacted according to example 2.

EXAMPLE 5

903 g of an aqueous saccharide/HMF-mixture with 7.8% HMF and a refractive index of 1.387, as it is obtained from a reaction in an autoclave (90% fructose, 10% glucose and other saccharides; d. s.) is neutralized with calcium hydroxide to pH 6.7, filtered and fed to a 10 l chromatographic column. In this column (diameter 8 cm, length 200 cm) is the resin Lewatit TSW 40 of BAYER in $Ca^{2+}$-form The column and the elution water have a temperature of 65° C.; the flow-rate is 10 l/h. The resulting elution diagram is shown in FIG. 2.

The saccharide fraction contains 152,4 g of saccharides, thereof 87% as fructose and 13% as glucose. The HMF-fraction yields, after concentration in vacuum, 55 g with a purity of 95%. That makes 78% of HMF present in the amount fed.

EXAMPLE 6 1598 g of a solution neutralized with ion exchanger and a refractive index of 1.3834 (HMF-content 3.9%) are chromatographed in a 10 l column, containing Lewatit TSW 40 in $Na^+$-form (diameter 8 cm, length 200 cm); the temperature is 65° C. and the flow rate 10 l/h. The solely HMF-containing fractions are concentrated and yield 50.0 g HMF in crystalline form. Related to the amount fed, 80% of HMF is obtained so.

EXAMPLE 7

The HMF fractions of two large-scale chromatographic separations in a three-column equipment with 13 m³ capacity of a cation exchange resin on polystyrene sulfonic acid basis in $Ca^{2+}$-form (fraction a: 143 kg d.s., thereof 137 kg HMF, 1 kg fructose, 4.6 kg other saccharides, fraction b: 176 kg d.s., thereof 163 kg HMF, 3.0 kg fructose, 1.9 kg glucose and 7.7 kg other saccharides) are concentrated below 80° C. in vacuum, until the remaining water-content of about 7% is reached. In a cooled, stirrer-crystallizer is crystallized in a multistage manner.

In the 1. crystallization, the mixture is cooled down from 20° C. with a cooling rate of 5° /h; at 10° C. the mass is seeded with HMF-crystals and further cooled to 4° C..

The obtained crystal-containing syrup is separated by centrifugal filtration in 124.5 kg crystals and 210.9 kg mother liquor (yield of crystals 39%). The crystals have a purity of 97% and are yellow colored.

The mother liquor contains, related to d.s., 88.4% HMF and 11.6% saccharides, and altogether 17% water. The water content can be determined via KF-titration with Hydranal Composite 5 K for ketones and Hydranal-Arbeits-medium K for ketones of Riedel-de Haen. The mother liquor is, after concentration to a final water-content of 3%, subjected to a second crystallization, and separated in 99 kg crystals and 111 kg mother liquor by centrifugal separation. The mother liquor is rechromatographed.

EXAMPLE 8 124 kg crystallized HMF (97%) is liquefied by gentle warming and filtered in a pressure nutsche filter, where 1 kg unsoluble solid is separated. Subsequently, the syrup is cooled to 5° C. in a cooled stirrer-crystallizer, as described in example 7, the magma is centrifuged; 45 kg crystals are obtained. The mother liquor and the wash-water are again cooled to 0° C as above described, the magma centrifuged and 25.5 kg crystals are obtained. The mother liquor is in a third crystallization step, as above described, cooled to −5° C. and the magma centrifuged, yielding 12.2 kg crystals. The total amount of crystalline HMF is 82.7 kg with a purity of 99.4%. The yield of crystals is 67%. The crystals have a faint yellow colour.

Altogether, 50 kg mother liquor is obtained, which are crystallized analogous to example 7.

EXAMPLE 9

Instead of a crystallization by cooling, it is possible to concentrate HMF-fractions, which are obtained in a chromatography as in example 7, to a final water content of 20-25% in vacuum below 80° C., and to let cool the syrup to 10° C. in a cooled stirrer-crystallizer.

With stirring and keeping the temperature constant, the crystallizer is carfully set under vacuum, which is adjustable, between 5 and 100 mbar. At a water content of 10% seeding crystals are added and the grown crystals are separated from the mother liquor analogous to example 7, when the magma has a crystal content of app. 50%.

I claim:

1. A process for preparing pure 5-hydroxymethylfurfuraldehyde (HMF) comprising the steps:
   (a) decomposing a saccharide in an aqueous solution in the presence of an acid catalyst and at a temperature of above 100° C. to produce a reaction product comprising a hexose and HMF;
   (b) chromatographically separting the aqueous reaction product at a temperature of 35° to 95° C. on a column of cation exchange resin to obtain a substantially hexose-containing fraction, an intermediate fraction containing hexose and HMF, and a substantially HFM-containing fraction;
   (c) returning the substantially hexose-containing fraction to step (a);
   (d) returning the intermediate fraction to the step (b); and
   (e) recovering pure HMF from the substantially HMF-containing fraction.

2. A process according to claim 1, further comprising effecting step (a) in the presence of an organic solvent, and removing the organic solvent from the reaction product prior to step (b).

3. A process according to claim 1, wherein the saccharide is fructose, a fructose-containing mixture or a fructose containing oligo-or polysaccharide.

4. A process according to claim 1, wherein the concentration of the saccharide in the aqueous solution is between 10 and 50% d.s.

5. A process according to claim 4 wherein the concentration of the saccharide is 30 to 40% d.s.

6. A process according to claim 1, wherein the acid catalyst is oxalic acid or sulfuric acid.

7. A process according to claim 6, wherein the concentraion of the acid is between 0.1 and 5%.

8. A process according to claim 1, wherein solids are separated from the reaction product of step (a) prior to step (b).

9. A process according to claim 1, wherein the cation exchange resin is in hydrogen form.

10. A process according to claim 1, wherein the reaction product is neutralized prior to step (b) and the cation exchange resin is in salt form.

* * * * *